US012089896B2

United States Patent
Velghe et al.

(10) Patent No.: US 12,089,896 B2
(45) Date of Patent: Sep. 17, 2024

(54) DEVICE AND METHOD FOR PLACING A PHOROPTER HEAD IN A HORIZONTAL POSITION

(71) Applicant: ESSILOR INTERNATIONAL, Charenton-le-pont (FR)

(72) Inventors: Julien Velghe, Charenton-le-pont (FR); Vincent Tejedor Del Rio, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 660 days.

(21) Appl. No.: 17/295,156

(22) PCT Filed: Nov. 20, 2018

(86) PCT No.: PCT/IB2018/001447
§ 371 (c)(1),
(2) Date: May 19, 2021

(87) PCT Pub. No.: WO2020/104827
PCT Pub. Date: May 28, 2020

(65) Prior Publication Data
US 2022/0007930 A1      Jan. 13, 2022

(51) Int. Cl.
*A61B 3/028*     (2006.01)
*A61B 3/00*      (2006.01)

(52) U.S. Cl.
CPC .......... *A61B 3/0285* (2013.01); *A61B 3/0008* (2013.01); *A61B 3/0075* (2013.01)

(58) Field of Classification Search
CPC ... A61B 3/0285; A61B 3/0008; A61B 3/0075; A61B 3/0041

USPC ......................................................... 351/222
See application file for complete search history.

(56) References Cited

U.S. PATENT DOCUMENTS

| 2008/0212029 | A1 | 9/2008 | Ichikawa | |
|---|---|---|---|---|
| 2008/0246922 | A1* | 10/2008 | Blum | A61B 3/04 351/233 |
| 2008/0309877 | A1 | 12/2008 | Saito | |
| 2010/0110379 | A1* | 5/2010 | Zhou | A61B 3/103 351/205 |

(Continued)

FOREIGN PATENT DOCUMENTS

| CN | 101322643 A | 12/2008 |
|---|---|---|
| CN | 202981955 U | 6/2013 |

(Continued)

OTHER PUBLICATIONS

International Search Report and Written Opinion of the ISA for PCT/IB2018/001447 dated Sep. 9, 2019, 13 pages.

(Continued)

*Primary Examiner* — Mohammed A Hasan
(74) *Attorney, Agent, or Firm* — NIXON & VANDERHYE

(57) ABSTRACT

Disclosed is a device for placing a phoropter head in a horizontal position in order to optimize the measurement of the visual acuity of a patient, and to a method for placing a phoropter head in a horizontal position. The device and method help performing a correct measurement of a patient's visual acuity by allowing the fine adjustment of the phoropter head horizontality and alerting when its position is not correct.

20 Claims, 3 Drawing Sheets

(56) References Cited

U.S. PATENT DOCUMENTS

2012/0287398 A1* 11/2012 Baker .................... A61B 3/103
  351/201
2016/0270656 A1* 9/2016 Samec ................... A61B 3/022
2018/0136486 A1* 5/2018 Macnamara ......... G02B 27/017

FOREIGN PATENT DOCUMENTS

| | | |
|---|---|---|
| CN | 106618580 A | 5/2017 |
| CN | 108762148 A | 11/2018 |
| EP | 2695578 A1 | 2/2014 |
| EP | 3075317 A1 | 10/2016 |
| JP | 2001-275967 A | 10/2001 |
| JP | 2007-61380 | 3/2007 |
| JP | 2008-212308 A | 9/2008 |
| JP | 2015-064700 A | 4/2015 |
| KR | 20020084865 A | 11/2002 |
| KR | 10-1128296 | 3/2012 |
| KR | 101128296 B1 * | 3/2012 |
| KR | 10-2016-0037438 | 4/2016 |
| WO | 2015/107303 | 7/2015 |
| WO | 2016178237 A1 | 11/2016 |

OTHER PUBLICATIONS

Office Action issued in Japanese Patent Application No. 2021-527951 dated Oct. 31, 2022.
Office Action, issued in Chinese Patent Application No. 201880099613.1 dated Apr. 12, 2024.

* cited by examiner

DEVICE AND METHOD FOR PLACING A PHOROPTER HEAD IN A HORIZONTAL POSITION

This application is the U.S. national phase of International Application No. PCT/IB2018/001447 filed Nov. 20, 2018 which designated the U.S., the entire contents of which are hereby incorporated by reference.

TECHNICAL FIELD OF THE INVENTION

The present invention relates to the field of optometry.

It more particularly relates to a device for placing a phoropter head in a horizontal position in order to optimize the measurement of the visual acuity of a patient, and to a method for placing a phoropter head in a horizontal position.

TECHNICAL BACKGROUND AND PRIOR ART

The necessary correction for compensating an individual's ametropia is generally determined by an optometrist or an ophthalmologist using a test known as "subjective refraction", during which the individual looks through a refraction apparatus adapted to generate a variable correction.

Such a refraction apparatus may be a phoropter. In the context of determining the necessary correction for compensating a patient's ametropia, one important parameter for a precise measurement is the patient's position relative to the measurement device and/or to the optotype.

Among the position adjustments that can be performed for optimizing determination of the necessary correction, one can cite the position of the patient, in particular the position of the patient's eyes, relative to the measurement device, but also the position, in particular the horizontality, of the measurement device by itself. It is important, at the beginning of the measurement, to position the phoropter as horizontally as possible. It is then also important to maintain the phoropter as horizontal as possible and avoid its position drifts for the whole duration of the visual acuity measurement, to ensure a correct determination of the necessary correction.

Some existing phoropters present functionality for adjusting their horizontality. However, this functionality is classically implemented with a device as simple as a spirit level. If such a device allows coarse identification of the horizontal position, it is however not appropriate for alerting if the position is not correct and only affords a coarse adjustment. There thus remains a need for devices allowing optimization of the horizontal position of the phoropter, in particular devices allowing a fine adjustment of its horizontality, and able to alert if the position is not correct.

SUMMARY OF THE INVENTION

In this context, the present invention proposes a device and a method for placing a phoropter head in a horizontal position in order to optimize the measurement of the visual acuity of a patient.

The first object of the invention is a device for placing a phoropter head in a horizontal position, comprising:
- a module for determining an angular deviation between a main plane of said phoropter head and a reference horizontal plane,
- a sensory indicator adapted to emit a sensory signal,
- a command unit programmed to activate said sensory indicator as a function of the angular deviation determined by said module in order to:

provide an adjustment sensory signal as long as said angular deviation is outside a first deviation range including the deviation of zero value, said first deviation range having a width superior or equal to zero, and, after said angular deviation has entered said first deviation range, provide a stop sensory signal as long as said angular deviation remains within a second deviation range, said second deviation range encompassing said first deviation range.

The device of the invention allows an optimal positioning of the phoropter head for the whole duration of the measurement of the visual acuity of a patient, by both allowing the fine adjustment of the phoropter head horizontality and alerting when the position is not correct. In addition, when the phoropter head comprises a power-variable liquid lens, maintaining a correct horizontal position of the phoropter head is important in case one wants to minimize the optical aberrations introduced by the deformation of the membrane under the action of gravity.

An initial adjustment of the phoropter head with the highest level of precision is undeniably important in regard to the precision of the visual acuity measurement.

However, even with careful manipulation, one cannot exclude that during the measurement and the associated motion of the phoropter head, its horizontality slightly drifts. If the level of precision of the horizontality maintaining and alerting during the whole measurement is as high as that for the first adjustment, the device may be in alert even if very small moves of the phoropter head are performed.

In the present invention, defining two different angular deviation ranges simultaneously affords a highest precision initial adjustment of the phoropter head, and a higher tolerance of the alerting system. Once the initial adjustment is performed, the alerting system will be triggered only if the angular deviation drifts too much from the initially adjusted angular position.

Other advantageous and non-limiting features of the device according to the invention include:
- The command unit is programmed to activate said sensory indicator as a function of the angular deviation determined by said module in order to, after said angular deviation has entered said first deviation range:
  provide a stop sensory signal if the current value of the angular deviation is inside the second deviation range, said stop sensory signal being provided even if the current value of the angular deviation is outside the first deviation range, and
  provide an adjustment sensory signal if the current value of the angular deviation is outside said second deviation range, but not if the current value of the angular deviation is inside said second deviation range, even if the current value of the angular deviation is outside the first deviation range.
- The adjustment sensory signal is representative of the direction and/or angular value of the position adjustment of the phoropter head needed in order to bring said angular deviation closer to said first deviation range;
- The stop sensory signal indicates that no further position adjustment of the phoropter head is needed;
- The adjustment sensory signal and the stop sensory signal comprise one or several in combination of the following types of signal: visual, haptic or aural signals;
- The sensory indicator comprises at least two sensory indicator elements, each located on a different side of a median vertical plane of the phoropter head;

Each sensory indicator element comprises a light source, and the command unit is programmed to make the light source located on the side towards which the phoropter head should be inclined in order to bring said angular deviation closer to said first deviation range blink to provide said adjustment visual signal;

The blink frequency or intensity of the light source during the adjustment visual signal is related to a current value of the angular deviation determined by the module;

The command unit is programmed to turn on or off both light sources to provide the stop visual signal;

The first deviation range is comprised between −0.1 and +0.1 degree;

The second deviation range is comprised between −0.2 and +0.2 degree;

The phoropter head comprises an optical system including a tunable lens.

A further object of the invention is a method for placing a phoropter head in a horizontal position, comprising:
determining an angular deviation between a main plane of said phoropter head and a reference horizontal plane,
emitting a sensory signal as a function of the angular deviation in order to:
provide an adjustment sensory signal as long as said angular deviation is outside a first deviation range including the deviation of zero value, and,
after said angular deviation has entered said first deviation range, provide a stop sensory signal as long as said angular deviation remains within a second deviation range, said second deviation range encompassing said first deviation range.

Another advantageous and non-limiting feature of the invention is a method for placing a phoropter head in a horizontal position, comprising:
a step of detecting a current value of an angular deviation between a main plane of said phoropter head and a reference horizontal plane,
a step of performing a first comparison by comparing the current value of the angular deviation detected in the detection step and a first deviation range, said first deviation range including the deviation of zero value and having a width superior or equal to zero,
a step of, based on the first comparison of the previous step, providing an adjustment sensory signal if said detected current value of the angular deviation is outside said first deviation range,
a step of, with guidance from the adjustment sensory signal provided in the previous step, modifying the angular deviation to bring its current value closer to the first deviation range if the current value of the angular deviation is outside the first deviation range,
repeating all previous steps until the current value of the angular deviation is inside the first deviation range,
after the current value of the angular deviation is inside the first deviation range, a step of performing a second comparison by comparing the current value of the angular deviation and a second deviation range encompassing the first deviation range;
based on the second comparison,
providing a stop sensory signal and returning to said second comparison step if the current value of the angular deviation is inside the second deviation range, said stop sensory signal being provided even if the current value of the angular deviation is outside the first deviation range,
providing an adjustment sensory signal and returning to said first comparison step if the detected current value of the angular deviation is outside said second deviation range, but not if the detected current value of the angular deviation is inside said second deviation range, even if the current value of the angular deviation goes outside the first deviation range.

BRIEF DESCRIPTION OF THE DRAWINGS

Various inventive features described herein are set forth with particularity in the appended claims. A better understanding of various features and advantages described herein will be obtained by reference to the following detailed description that sets forth illustrative embodiments and the accompanying drawings of which:

DETAILED DESCRIPTION

Figure 1:
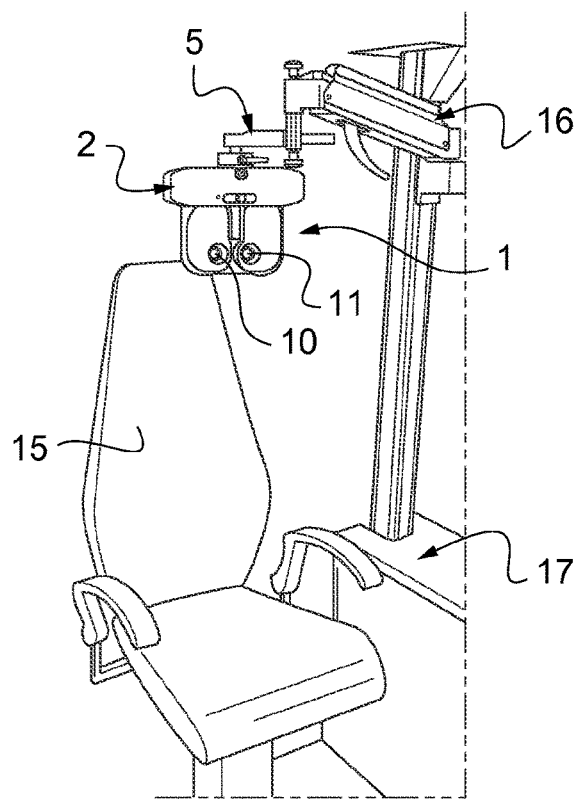
FIG. 1 illustrates the use of a phoropter head for a visual acuity measurement.

The following description with reference to the accompanying drawings will make it clear what the invention consists of and how it can be achieved. The invention is not limited to the embodiments illustrated in the drawings. Accordingly, it should be understood that where features mentioned in the claims are followed by reference signs, such signs are included solely for the purpose of enhancing the intelligibility of the claims and are in no way limiting on the scope of the claims.

Figure 2:
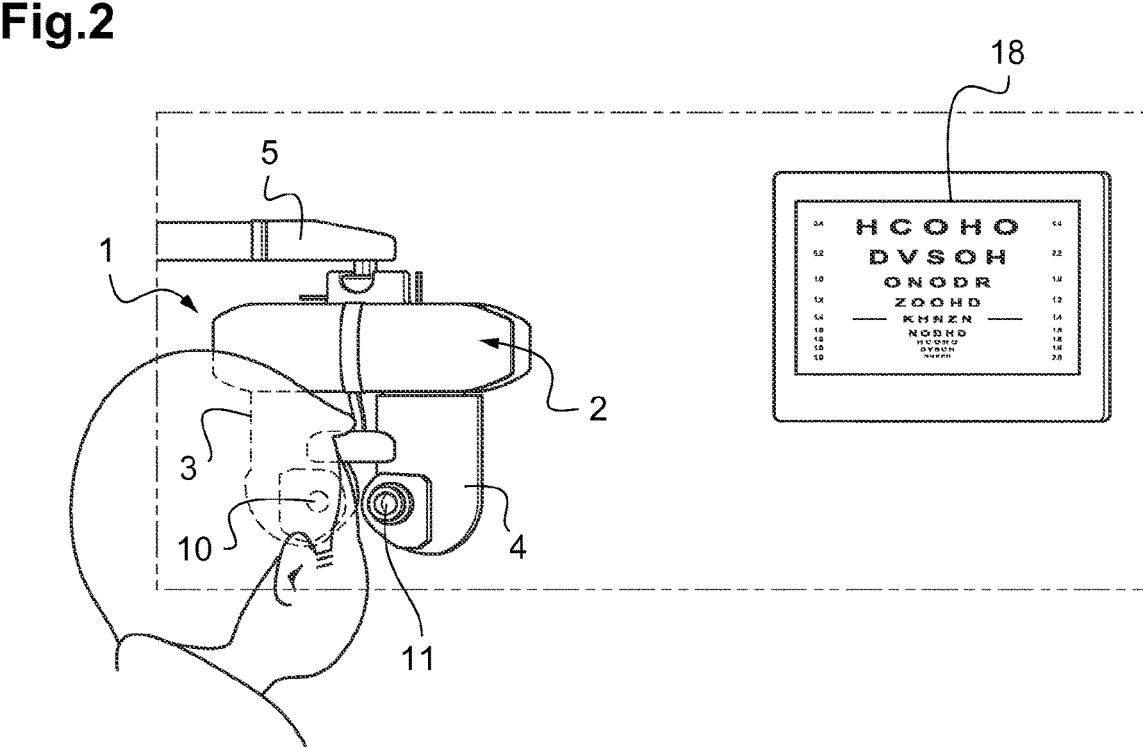
FIG. 2 illustrates the relative position of a phoropter head and an optotype during a visual acuity measurement.

FIGS. 1 and 2 show the context for using a phoropter head 1 for determining refractive properties or refractive correction need of an eye of a subject who is a wearer of corrective eyeglasses or contact lenses whose correction needs are to be assessed. The phoropter head 1 is mounted on a holder 5 which is further linked to a hinged arm 16. The hinged arm 16 is further attached to a stationary portion of the phoropter 17. When assessing the correction needs of the patient, said patient is seated in a seat 15, and the eyepieces 10, 11 of the phoropter head 1 are placed in front of the patient's eyes. The patient's correction needs are evaluated based on the aptitude of the patient to identify the characters displayed on an optotype 18 when he looks through the optical systems arranged behind the eyepieces 10, 11.

Figure 3:
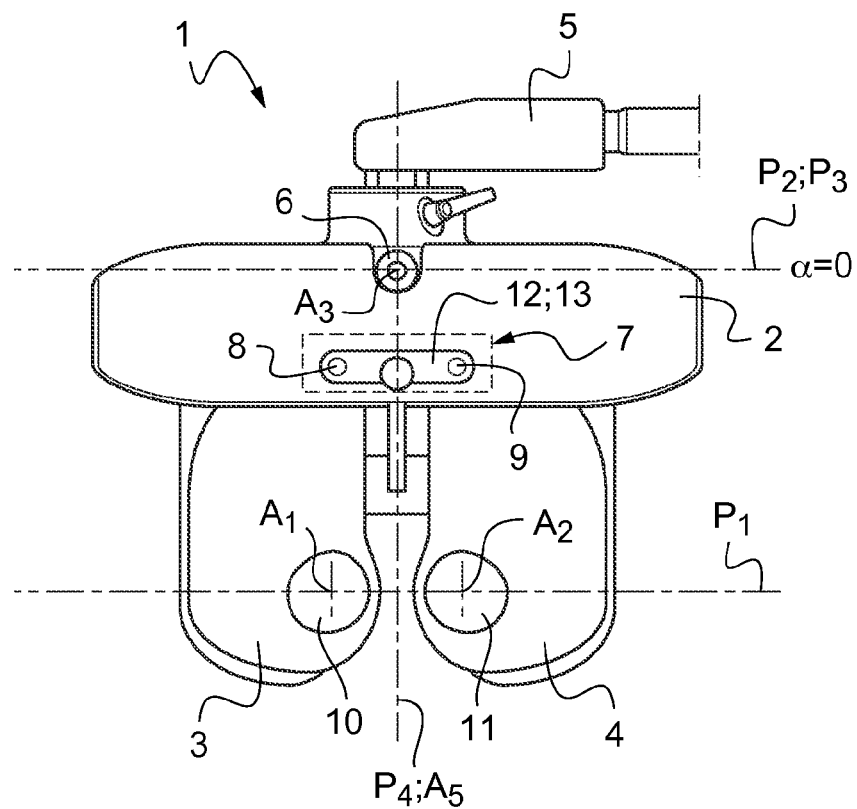
FIG. 3 illustrates a phoropter head comprising a device according to the invention.
Figure 4:
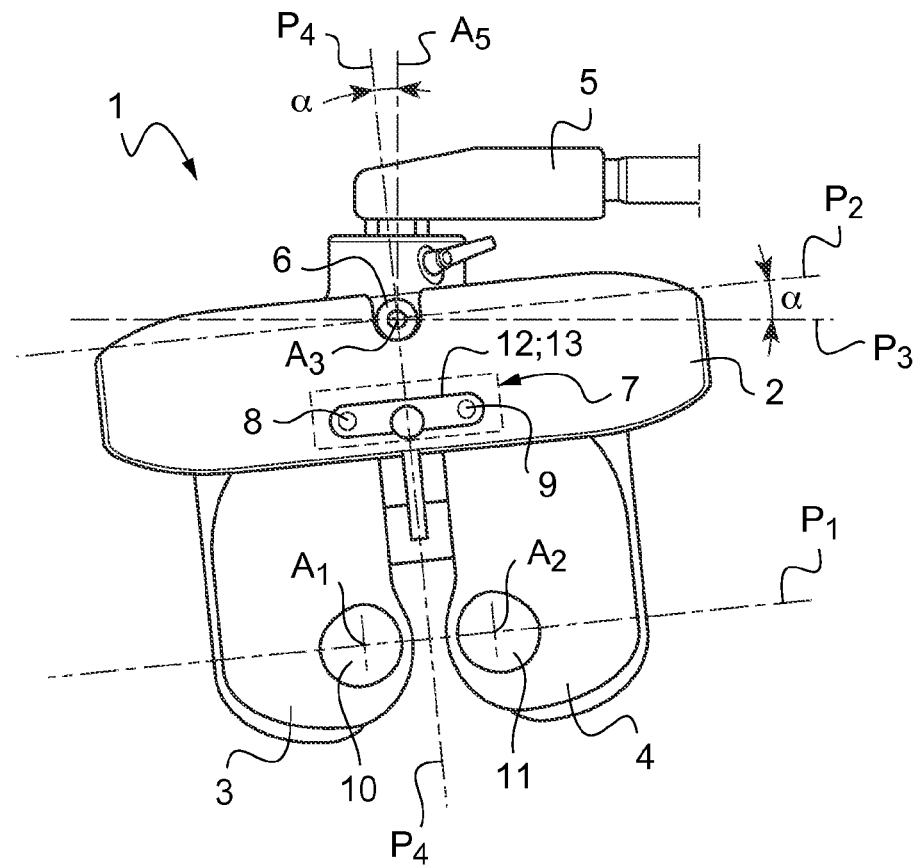
FIG. 4 illustrates the angular deviation to be measured between a main plane of the phoropter head and a reference horizontal plane according to the invention.

FIGS. 3 and 4 more precisely show the different parts and the position of the phoropter head 1. This phoropter head 1 has a median plane of symmetry P4 which, in use, is intended to be substantially vertical. The phoropter head 1 comprises an upper housing 2 carrying two lower barrels 3, 4 configured to receive the gaze of both eyes of the subject under examination and thus forming a binocular vision assembly. The two lower barrels 3, 4 are arranged symmetrically to each other in relation to the plane P4 and each barrel 3, 4 comprises an optical system (not shown) arranged behind an eyepiece 10, 11 having a horizontal optical axis A1, A2 respectively. Each optical system advantageously includes a tunable lens (not shown), such as disclosed in WO2015107303, to apply a variable focal power to the optical path observed by the corresponding eye. The pupillary distance between axes A1 and A2 is adjustable.

The upper housing 2 of the phoropter head 1 is mounted on a holder 5 via a pivot linkage 6 allowing the housing 2 to pivot about a horizontal pivot axis A3 parallel to the optical axes A1, A2 of the eyepieces 10, 11. The linkage between the phoropter head 1 and the holder 5 further allows the phoropter head 1 to pivot about a vertical axis A5.

According to the invention, the phoropter head 1 further comprises an adjustment device 7 for placing the head 1 of the phoropter in a predetermined horizontal position.

More precisely, we define:
a gaze plane P1 containing the optical axes A1 and A2 of the eyepieces 10, 11, said gaze plane P1 being perpendicular to the median plane of symmetry P4,
an adjustment main plane P2 containing the pivot axis A3 and parallel to said gaze plane P1, said adjustment main plane P2 being perpendicular to the median plane of symmetry P4,
a reference horizontal plane P3 which is horizontal and contains the pivot axis A3.

The adjustment device 7 comprises a module 12 for determining an angular deviation α which is, as illustrated in FIG. 4, the angle formed between the adjustment main plane P2 of said phoropter head 1 and the reference horizontal plane P3.

The adjustment device 7 further comprises a sensory indicator adapted to emit a sensory signal. In the example illustrated by FIGS. 3 and 4, this sensory indicator is a visual indicator adapted to emit a visual signal. The visual indicator comprises two light-emitting diodes 8 and 9 as sensory indicator elements each symmetrically located on both sides of the median vertical plane P4 of the phoropter head 1. Said visual signal can be the turning on or off of at least one light-emitting diode 8, 9, the blinking of at least one light-emitting diode 8, 9, the change in blink frequency of at least one light-emitting diode 8, 9, the change of intensity of at least one light-emitting diode 8, 9, and/or the color change of at least one light-emitting diode 8, 9.

According to one envisionable variant, the sensory signal could be a haptic signal, such as the turning on or off of a vibration or a mechanical impulsion and/or an aural signal, such as the turning on or off of a sound or the change of intensity or frequency of a sound.

The adjustment device 7 of FIG. 3 comprises two sensory indicator elements 8 and 9. Alternatively, adjustment device 7 can comprise one single sensory indicator element or more than two sensory indicator elements. Each sensory indicator element can be a light source, such as a light-emitting diode, a sound source, and/or a vibration source.

The phoropter head 1 further comprises a command unit 13 programmed to activate the sensory indicator elements 8, 9 as a function of the angular deviation α determined by said module.

More precisely, the command unit 13 is programmed to activate the sensory indicator elements 8, 9 in order to provide an adjustment sensory signal as long as said angular deviation α is outside a first deviation range. This first deviation range includes the deviation of zero value and has a width superior or equal to zero.

The command unit 13 is further programmed to activate, after said angular deviation α has entered said first deviation range, the sensory indicator elements 8, 9 in order to provide a second sensory signal as long as said angular deviation α remains within a second deviation range. This second deviation range encompasses said first deviation range.

The first and second deviation ranges define two different ranges of acceptable values for the angular deviation α between the main plane P2 of the phoropter head 1 and the reference horizontal plane P3 during two different phases of the measurement of visual acuity.

The first deviation range represents a range of acceptable values for the angular deviation α of the phoropter head 1 at the beginning of the measurement of visual acuity. In this first phase, the adjustment device 7 allows finely reaching a correct horizontal position of the main plane P2 of the phoropter head 1 and alerting as long as said horizontal position is not reached. The first deviation range includes the deviation of zero value.

In an embodiment, the first deviation range has a width of zero, meaning that it comprises only the zero value. This means that the highest level of precision is first needed when adjusting the phoropter head 1, subject to the angle measurement precision.

In some embodiments, the first deviation range is symmetrical about the zero value, meaning that the width of the range that is lower than zero is equal to the width of the range that is higher than zero. In other embodiments, the first deviation range is not symmetrical about the zero value.

In an embodiment, the first deviation range is comprised between −0.1 and +0.1 degree, preferably between −0.05 and +0.05 degree.

The second deviation range represents a range of acceptable values for the angular deviation α of the phoropter head 1 during the measurement of visual acuity once the first deviation range has been reached. In this second phase, the adjustment device 7 allows monitoring the drift of the phoropter head 1 from the horizontal position that has been set in the first phase, and alerting if said drift is too important. The second deviation range includes the deviation of zero value.

The second deviation range is wider than the first deviation range and encompasses said first deviation range.

In some embodiments, the second deviation range is symmetrical about the zero value. In other embodiments, the second deviation range is not symmetrical about the zero value.

In an embodiment, the second deviation range is comprised between −0.2 and +0.2 degree.

The adjustment sensory signal is advantageously representative of a position adjustment of the phoropter head 1, in particular representative of the direction and/or angular value of the angular position adjustment of the phoropter head 1 needed in order to bring the angular deviation α closer to the first deviation range.

It should be understood that a value is «inside» a range if the value is comprised between the minimum and maximum of the range, or equal to the minimum or the maximum of the range. A value is «outside» a range if it is not inside said range.

Bringing a parameter «closer to» a range means reducing the absolute value of the difference between the parameter value and the minimum and/or the maximum of said range. Bringing a parameter «closer to» a range includes bringing the parameter value inside said range. The value of the parameter that is brought «closer to» a range is initially outside said range.

Bringing the angular deviation α closer to a deviation range may be performed manually by the operator, for instance by manually tilting the phoropter head 1 about the horizontal pivot axis A3, or by the intermediate of a controlling device such as a motor, an actuator or a micrometer screw. The set point value may be communicated to the controlling device either directly by the operator, or automatically via an associated computer.

The stop sensory signal indicates that no further position adjustment of the phoropter head 1 is needed.

In an embodiment, the adjustment sensory signal and the stop sensory signal emitted by the sensory indicator elements 8 and 9 are both visual signals. Alternatively, the adjustment sensory signal and the stop sensory signal can be of different types (visual, aural and/or haptic).

For example, as shown in FIGS. 3 and 4, the sensory indicator comprises two light sources 8 and 9, each located on a different side of the median plane P4 of the phoropter head 1. The command unit 13 is programmed to make the light source 8 or 9 located on the side towards which the phoropter head 1 should be inclined in order to bring the angular deviation α closer to said first deviation range blink to provide said adjustment visual signal.

The intensity and/or the blinking frequency of the visual signal emitted by the sensory indicator elements 8, 9 is representative of the angular value of the position adjustment of the phoropter head 1 needed in order to bring the angular deviation α closer to the first deviation range. For instance, the further the angular deviation α is from the first deviation range, the lower the visual signal intensity is, or the lower the visual signal blink frequency is.

When the sensory signal is a vibration, the intensity and/or the frequency of the vibration can be similarly representative of the angular value of the position adjustment of the phoropter head 1 needed in order to bring the angular deviation α closer to the first deviation range.

When the sensory signal is a sound, the intensity and/or the frequency of the sound can be similarly representative of the angular value of the position adjustment of the phoropter head 1 needed in order to bring the angular deviation α closer to the first deviation range.

The command unit 13 is programmed to emit and when necessary to change the sensory signal as detailed above. The command unit 13 is advantageously programmed to turn on or off at least one of both light sources 8 and 9 to provide the stop visual signal, preferably to turn on both light sources 8 and 9 to provide the stop visual signal. Alternatively, the command unit can be programmed to change color of at least one of both light sources 8 and 9 to provide the stop visual signal.

Figure 5:
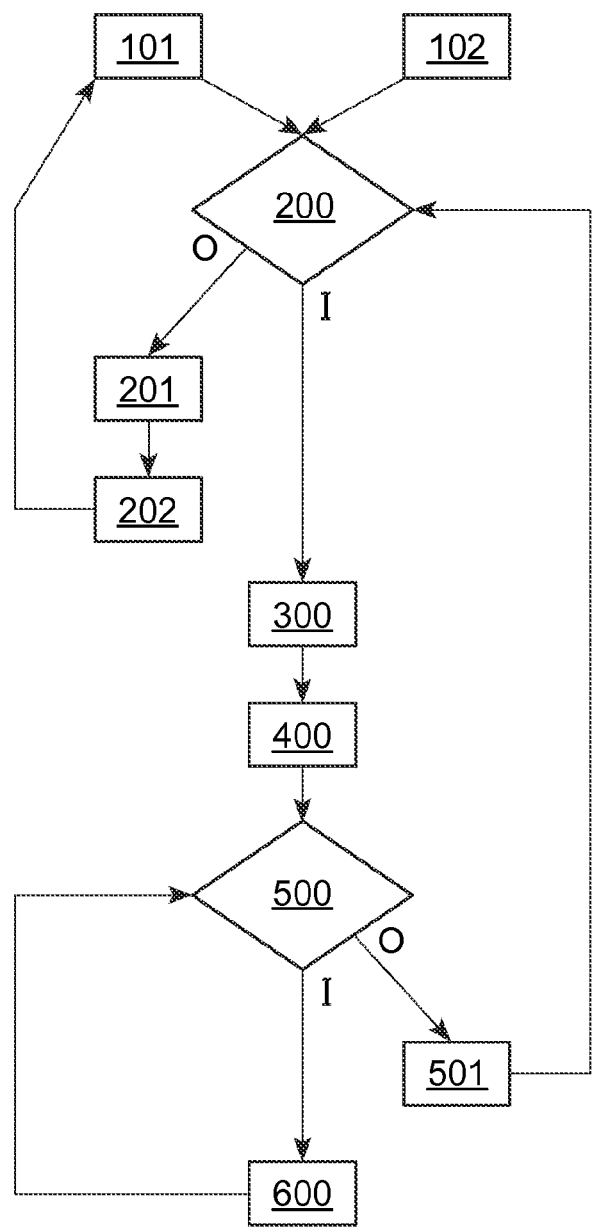
FIG. 5 illustrates a method for placing a phoropter head in a horizontal position according to the invention.

FIG. 5 shows the steps of a method for placing a phoropter head 1 in a horizontal position according to the invention.

The method comprises a first step 101 of detecting a current value of the angular deviation α between the main plane P2 of said phoropter head 1 and the reference horizontal plane P3.

Simultaneously or before of after the determination of step 101, the first deviation range is provided in a step 102.

A comparison 200 between the measured angular deviation α and the first deviation range may lead to the conclusion that the angular deviation α is outside (O) or inside (I) the first deviation range.

Based on the comparison 200, an adjustment sensory signal is provided in a step 201 if the current value of the angular deviation α is outside the first deviation range. In that case, the angular deviation α is brought inside the first deviation range in a step 202. With guidance from the adjustment sensory signal, the angular deviation α is modified, manually or automatically with an inboard motorized actuator, to bring its current value closer to the first deviation range.

Steps 101, 200, 201, 202 are repeated until the current value of the angular deviation α is inside the first deviation range.

Once the angular deviation α is inside the first deviation range, no more first adjustment signal is provided in a step 300 and a stop signal is provided. The phoropter head 1 is then in a correct working angular position and the refraction measurement can be performed.

However, after the angular deviation α has reached the first deviation range, the control of the angular deviation α continues. The goal is then to control if the angular deviation α is maintained inside the second deviation range which is broader than the first deviation range. Angular deviations inside the second deviation range are thus tolerated during the refraction measurement is performed.

For this purpose, the second deviation range is provided in a step 400. In a step 500, the current value of the angular deviation α is still determined and a comparison between the measured angular deviation α and the second deviation range is performed. Said comparison may lead to the conclusion that the angular deviation α is outside (O) or inside (I) the second deviation range.

If the angular deviation α detected at this specific moment by the module 12 is outside the second deviation range, no more stop signal is provided in step 501.

For this purpose, based on the comparison of step 500, a stop sensory signal is provided in a step 600 if the current value of the angular deviation α remains inside the second deviation range. The stop sensory signal is provided even if the current value of the angular deviation α goes outside the first deviation range. Determination of the current value of the angular deviation α and comparison step 500 is repeated as long as the horizontal position of the phoropter head 1 is needed.

Based on the comparison of step 500, an adjustment sensory signal is provided in a step 501, if the current value of the angular deviation α goes outside said second deviation range. But no adjustment sensory signal is provided as long as the current value of the angular deviation α remains inside said second deviation range, even if the current value of the angular deviation α goes outside the first deviation range.

In that case (if the current value of the angular deviation α goes outside said second deviation range), the angular deviation α is brought inside the first deviation range by returning to comparison step 200. With guidance from the adjustment sensory signal, the angular deviation α is modified, manually or automatically with an inboard motorized actuator, to bring its current value closer to the first deviation range. Steps 101, 200, 201, 202 are thus repeated until the current value of the angular deviation α is inside the first deviation range.

Bringing the angular deviation inside the first deviation range at step 202 can be performed by repeating the previous steps until the angular deviation α is inside the first deviation range and no more first adjustment signal is provided in step 300.

Bringing the angular deviation α inside the second deviation range at step 502 can be performed by repeating the steps following the determination of the second deviation range until the angular deviation α is inside the second deviation range and the second stop signal is provided in step 300.

Steps 500 to 600 are repeated as long as the phoropter head 1 needs remaining horizontal.

A «current angular deviation value« or «current value» refers to a value of the angular deviation α at a specific moment. Thus, this «current value» may change as the method of the invention is being implemented. For instance, the current angular deviation value that is detected in step 500 may be different from the current angular deviation value that was detected in step 101. Similarly, the current angular deviation value that is detected when step 101 or 500 is repeated may be different from the current angular deviation value that was respectively detected in previous step 101 or 500.

Comparing an angular deviation value and a deviation range consists in determining whether the angular deviation value is inside said range, which means comprised between the minimum and maximum values of said range. As previously mentioned, if the angular deviation is equal to the minimum or maximum value of the range, it is considered inside the range.

If the measured angular deviation α is inside the first deviation range at step 200, instead of providing no more first adjustment signal in step 300, the sensory indicator can emit an adjustment signal different from that emitted when the measured angular deviation α is outside the first deviation range.

If the measured angular deviation α is outside the second deviation range at step 500, instead of providing no second stop signal in step 501, the sensory indicator can emit a stop signal different from that emitted when the measured angular deviation α is inside the second deviation range.

When two different sensory signals are emitted depending on if a detected angular deviation α value is inside or outside an angular deviation range, both different sensory signals are advantageously sufficiently different from each other for a user to easily detect if the current angular deviation value switches from inside to outside or from outside to inside said angular deviation range.

According to the present invention, «repeating» a group of steps as long as a condition is fulfilled means that the group of steps is implemented iteratively at a given frequency, and the iteration stops once the condition is no more fulfilled. The given frequency can be determined by the phoropter user or may be a fixed parameter.

Repetition of steps 101 to 300 allows the initial placement of the phoropter head 1 as close as possible to the horizontal position so as to begin the acuity measurement with a correct position. Repetition of steps 500 to 600 allows avoiding the angular deviation α drifting much from the correct position reached in step 300. Steps 500 to 600 are advantageously repeated for the whole duration of the visual acuity measurement.

If the measured angular deviation value α is inside the first deviation range at step 200, no modification of the angular deviation is necessary, steps 101 to 300 do not need to be repeated and step 300 is directly reached.

If the measured angular deviation value α is outside the second deviation range at step 500, no modification of the angular deviation is necessary and step 600 is directly reached.

Each characteristic described in a specific embodiment of the present invention can be combined with any other embodiment of the invention as long as it is not incompatible therewith.

The invention claimed is:

1. A device for placing a phoropter head in a horizontal position, the device comprising:
   one or more processors configured to determine an angular deviation between a main plane of said phoropter head and a reference horizontal plane;
   a sensory indicator adapted configured to emit a sensory signal; and
   a controller programmed to activate said sensory indicator as a function of the determined angular deviation to:
      provide an adjustment sensory signal as long as said angular deviation (a) is outside a first deviation range including the deviation of zero value, said first deviation range having a width greater than or equal to zero, and
      after said angular deviation has entered said first deviation range, provide a stop sensory signal as long as said angular deviation (a) remains within a second deviation range, said second deviation range being wider than the first deviation range and encompassing said first deviation range.

2. The device according to claim 1, wherein the controller is programmed to activate said sensory indicator as a function of the determined angular deviation order to, after said angular deviation (a) has entered said first deviation range:
   provide a stop sensory signal when the current value of the angular deviation is inside the second deviation range, said stop sensory signal being provided even when the current value of the angular deviation is outside the first deviation range, and
   provide an adjustment sensory signal when the current value of the angular deviation is outside said second deviation range, but not when the current value of the angular deviation is inside said second deviation range, even when the current value of the angular deviation is outside the first deviation range.

3. The device according to claim 1, wherein said adjustment sensory signal is representative of one or more of the direction and an angular value of the position adjustment of the phoropter head that brings said angular deviation closer to said first deviation range.

4. The device according to claim 1, wherein said stop sensory signal indicates that no further position adjustment of the phoropter head is needed.

5. The device according to claim 1, wherein said adjustment sensory signal and said stop sensory signal comprise one or more in combination of the following types of signal: visual, haptic or aural signals.

6. The device according to claim 1, wherein said sensory indicator comprises at least two sensory indicator elements, each of the at least two sensory indicator elements located on a different side of a median vertical plane of said phoropter head.

7. The device according to claim 6, wherein each of the sensory indicator elements comprises a light source, and
   wherein said controller is programmed to make the light source located on the side towards which the phoropter head is to be inclined in order to bring said angular deviation closer to said first deviation range blink to provide said adjustment visual signal.

8. The device according to claim 7, wherein the blink frequency or intensity of said light source during said adjustment visual signal is related to a current value of the determined angular deviation.

9. The device according to claim 7, wherein said controller is programmed to turn on or off both of the light sources to provide said stop visual signal.

10. The device according to claim 7, wherein said controller is programmed to change color of at least one of both of the light sources to provide said stop visual signal.

11. The device according to claim 1, wherein said first deviation range is comprised between −0.1 and +0.1 degree.

12. The device according to claim 1, wherein said second deviation range is comprised between −0.2 and +0.2 degree.

13. The device according to claim 1, wherein the phoropter head comprises an optical system including a tunable lens.

14. A method for placing a phoropter head in a horizontal position, the method comprising:
  determining an angular deviation between a main plane of said phoropter head and a reference horizontal plane; and,
  emitting a sensory signal as a function of the angular deviation in order to:
    provide an adjustment sensory signal as long as said angular deviation is outside a first deviation range including the deviation of zero value, and
    after said angular deviation has entered said first deviation range, provide a stop sensory signal as long as said angular deviation remains within a second deviation range, said second deviation range being wider than the first deviation range and encompassing said first deviation range.

15. The method for placing the phoropter head in the horizontal position according to claim 14, further comprising:
  detecting a current value of the angular deviation between the main plane of said phoropter head and the reference horizontal plane;
  performing a first comparison by comparing the detected current value of the angular deviation and the first deviation range, said first deviation range including the deviation of zero value and having a width greater than or equal to zero;
  providing the adjustment sensory signal when said detected current value of the angular deviation is outside said first deviation range, based on the first comparison;
  modifying the angular deviation to bring the current value of the angular deviation closer to the first deviation range when the current value of the angular deviation is outside the first deviation range, with guidance from the adjustment sensory signal;
  repeating the detecting, the performing the first comparison, the providing, and the modifying until the current value of the angular deviation is inside the first deviation range;
  after the current value of the angular deviation is inside the first deviation range, performing a second comparison by comparing the current value of the angular deviation to the second deviation range encompassing the first deviation range,
  based on the performing the second comparison,
    providing the stop sensory signal and returning to said performing the second comparison when the current value of the angular deviation is inside the second deviation range, said stop sensory signal being provided even when the current value of the angular deviation is outside the first deviation range,
    providing another providing adjustment sensory signal and returning to said performing the first comparison if when the detected current value of the angular deviation is outside said second deviation range, but not when the detected current value of the angular deviation is inside said second deviation range, even when the current value of the angular deviation (a) goes outside the first deviation range.

16. The device according to claim 2, wherein said adjustment sensory signal is representative of one or more of the direction and an angular value of the position adjustment of the phoropter head that brings said angular deviation closer to said first deviation range.

17. The device according to claim 2, wherein said stop sensory signal indicates that no further position adjustment of the phoropter head is needed.

18. The device according to claim 3, wherein said stop sensory signal indicates that no further position adjustment of the phoropter head is needed.

19. The device according to claim 2, wherein said adjustment sensory signal and said stop sensory signal comprise one or more in combination of the following types of signal: visual, haptic or aural signals.

20. The device according to claim 3, wherein said adjustment sensory signal and said stop sensory signal comprise one or more in combination of the following types of signal: visual, haptic or aural signals.

* * * * *